(12) United States Patent
Urbanski et al.

(10) Patent No.: US 10,820,925 B2
(45) Date of Patent: Nov. 3, 2020

(54) TRANSSEPTAL NEEDLE

(71) Applicant: Baylis Medical Company Inc., Montreal (CA)

(72) Inventors: John Paul Urbanski, Toronto (CA); Gareth Davies, Toronto (CA); Mahmood Mirza, North York (CA); Bogdan Beca, Thornhill (CA)

(73) Assignee: Baylis Medical Company Inc., Mississauga (CA)

( * ) Notice: Subject to any disclaimer, the term of this patent is extended or adjusted under 35 U.S.C. 154(b) by 626 days.

(21) Appl. No.: 15/160,737

(22) Filed: May 20, 2016

(65) Prior Publication Data

US 2016/0262795 A1  Sep. 15, 2016

Related U.S. Application Data

(60) Continuation-in-part of application No. 14/222,909, filed on Mar. 24, 2014, now Pat. No. 10,493,259.
(Continued)

(51) Int. Cl.
*A61B 18/18* (2006.01)
*A61B 17/34* (2006.01)
(Continued)

(52) U.S. Cl.
CPC ........ *A61B 17/3476* (2013.01); *A61B 5/0215* (2013.01); *A61B 5/6848* (2013.01); *A61B 18/1477* (2013.01); *A61M 1/008* (2013.01); *A61M 3/0283* (2013.01); *A61M 5/007* (2013.01); *A61M 5/32* (2013.01);
(Continued)

(58) Field of Classification Search
CPC ............ A61B 17/3476; A61B 17/3478; A61B 18/1477; A61B 18/1492; A61B 2017/00247; A61B 2017/00862; A61B 2017/00867; A61B 2018/00083; A61B 2018/00136; A61B 2018/00297; A61B 2018/00357; A61B 2018/00375; A61B 2018/00404; A61B 2090/064
See application file for complete search history.

(56) References Cited

U.S. PATENT DOCUMENTS 4,960,410 A * 10/1990 Pinchuk ............ A61M 25/0054
604/103.1
5,211,183 A  5/1993 Wilson
(Continued)

FOREIGN PATENT DOCUMENTS

WO  WO20033909 A1  6/2000
WO  WO2005046487 A  5/2005
WO  WO2013101632 A1  7/2013

*Primary Examiner* — Michael F Peffley
*Assistant Examiner* — Amanda L Zink
(74) *Attorney, Agent, or Firm* — Glenn Arnold; Vincent Man; Samuel Tekie (57) ABSTRACT

Methods and apparatus are disclosed for a needle comprising a distal shaft and a proximal shaft joined at a junction, the needle having a distal tip which includes an electrode for delivering energy to puncture a tissue, wherein the distal shaft is comprised of a superelastic material. In typical embodiments, the needle includes a lumen for delivering and withdrawing fluids from a treatment site. In some embodiments the junction is comprised of a superelastic material.

19 Claims, 8 Drawing Sheets

Related U.S. Application Data which is a continuation-in-part of application No. 13/468,939, filed on May 10, 2012, now Pat. No. 8,679,107, which is a division of application No. 11/905,447, filed on Oct. 1, 2007, now Pat. No. 8,192,425.

(60) Provisional application No. 60/884,285, filed on Jan. 10, 2007, provisional application No. 60/827,452, filed on Sep. 29, 2006.

(51) Int. Cl.
| | | |
|---|---|---|
| *A61M 3/02* | (2006.01) | |
| *A61M 5/32* | (2006.01) | |
| *A61M 1/00* | (2006.01) | |
| *A61B 18/14* | (2006.01) | |
| *A61M 39/08* | (2006.01) | |
| *A61M 5/00* | (2006.01) | |
| *A61B 5/00* | (2006.01) | |
| *A61B 5/0215* | (2006.01) | |
| *A61B 17/00* | (2006.01) | |
| *A61B 18/00* | (2006.01) | |
| *A61B 90/00* | (2016.01) | |
| *A61B 6/12* | (2006.01) | |

(52) U.S. Cl.
CPC ............... *A61M 39/08* (2013.01); *A61B 6/12* (2013.01); *A61B 17/3478* (2013.01); *A61B 18/1492* (2013.01); *A61B 90/02* (2016.02); *A61B 2017/00247* (2013.01); *A61B 2017/00862* (2013.01); *A61B 2017/00867* (2013.01); *A61B 2018/00083* (2013.01); *A61B 2018/00136* (2013.01); *A61B 2018/00297* (2013.01); *A61B 2018/00357* (2013.01); *A61B 2018/00375* (2013.01); *A61B 2018/00404* (2013.01); *A61B 2090/064* (2016.02); *A61B 2090/0811* (2016.02); *A61B 2090/3966* (2016.02); *A61B 2090/3983* (2016.02); *A61B 2218/002* (2013.01); *A61B 2218/007* (2013.01); *Y10T 29/49826* (2015.01)

(56) References Cited

U.S. PATENT DOCUMENTS

| | | | | |
|---|---|---|---|---|
| 5,364,393 | A * | 11/1994 | Auth | A61B 18/1492 606/34 |
| 6,607,529 | B1 * | 8/2003 | Jones | A61B 18/1477 606/40 |
| 8,500,697 | B2 | 8/2013 | Kurth et al. | |
| 2005/0101984 | A1 * | 5/2005 | Chanduszko | A61B 17/0057 606/185 |
| 2008/0146918 | A1 | 6/2008 | Magnin et al. | |
| 2008/0275439 | A1 | 11/2008 | Francischelli et al. | |
| 2009/0105742 | A1 | 4/2009 | Kurth et al. | |
| 2012/0232546 | A1 | 9/2012 | Mirza et al. | |
| 2013/0184551 | A1 * | 7/2013 | Paganelli | A61B 5/6847 600/377 |

\* cited by examiner

TRANSSEPTAL NEEDLE

CROSS-REFERENCE TO OTHER APPLICATIONS

This application is a CIP of U.S. application Ser. No. 14/222,909, filed Mar. 24, 2014, now U.S. Pat. No. 10,493,259, which is a continuation-in-part of U.S. application Ser. No. 13/468,939, filed on May 10, 2012, now U.S. Pat. No. 8,679,107, which is a divisional application of, and claims priority from, U.S. application Ser. No. 11/905,447, filed on Oct. 1, 2007, now U.S. Pat. No. 8,192,425, which claims the benefit of: U.S. provisional application No. 60/827,452, filed on Sep. 29 2006, and U.S. provisional application No. 60/884,285, filed on Jan. 10, 2007, all of which are incorporated by reference herein in their entirety.

All of the following patents and applications are incorporated herein by reference in their entirety: U.S. application Ser. No. 13/113,326, filed May 23, 2011; U.S. application Ser. No. 11/265,304, filed Nov. 3, 2005, now U.S. Pat. No. 7,947,040; U.S. application Ser. No. 10/666,301, filed Sep. 19, 2003, now issued as U.S. Pat. No. 7,048,733; U.S. application Ser. No. 10/760,479, filed Jan. 21, 2004, now issued as U.S. Pat. No. 7,270,662; U.S. application Ser. No. 10/666,288, filed Sep. 19, 2003; U.S. application Ser. No. 10/347,366, filed Jan. 21, 2003, now issued as U.S. Pat. No. 7,112,197; and U.S. provisional application 60/522,753, filed Nov. 3, 2004.

TECHNICAL FIELD

The disclosure generally relates to the field of medical devices and methods for accessing interior anatomy. More specifically, the disclosure relates to surgical needles.

BRIEF DESCRIPTION OF THE DRAWINGS

In order that the invention may be readily understood, embodiments of the invention are illustrated by way of examples in the accompanying drawings.

DETAILED DESCRIPTION

Some transseptal needles are comprised of separate proximal and distal shaft sections comprised of steel and joined at a shaft junction. This junction or joint where the proximal and distal shaft sections meet can bend or even break when mechanically loaded during use. For example, a distal shaft section can break when a physician loads the needle into a dilator, or when a physician bends a distal portion of the needle (manually or by using mechanical pliers) to create a distal curve. If the tip (or distal shaft) of a Brockenbrough/transseptal needle separates from the main/proximal shaft during a procedure, it may become lost inside of a patient.

It is desirable that a transseptal needle be resistant to unintentional permanent bending and fatigue failure at the junction of the proximal and distal shafts without compromising overall device performance.

The present inventors have conceived and reduced to practice embodiments of a surgical puncturing device, or needle assembly, wherein at least a part/portion of a distal shaft is superelastic. Such a distal shaft is more tolerant to stress than a similar sized distal shaft comprised of only non-superelastic material (e.g. steel). In most cases, when subjected to a mechanical load, the superelastic distal shaft of the invention bends but is less likely to plastically deform than a steel distal shaft. Furthermore, a superelastic distal shaft may be advanced through tight curves in dilators and anatomy without permanent deformation. In typical embodiments, the proximal shaft is comprised of standard (non-superelastic) materials used in surgical devices and known to those skilled in the art, which provide columnar strength for pushability to enable advancement of the needle through a puncture in the tissue. The columnar strength also provides for tactile feedback to a user of the device, as explained in detail in U.S. Pat. No. 8,192,425, "RADIOFREQUENCY PERFORATION APPARATUS", issued Jun. 5, 2012.

In one broad aspect, embodiments of the present invention include a needle comprising a distal shaft and a proximal shaft joined at a junction, the needle having a distal tip which includes an electrode for delivering energy to puncture a tissue, wherein the distal shaft is comprised of a superelastic material. In typical embodiments, the shaft includes a lumen for delivering and withdrawing fluids from a treatment site. Some embodiments of this broad aspect include a distal shaft comprised of both superelastic and non-superelastic material.

In another broad aspect, embodiments of the present invention include a needle comprising a distal shaft and a proximal shaft joined at a junction, the needle having a distal tip which includes an electrode for delivering energy to puncture a tissue, wherein the junction is comprised of a superelastic material. In some embodiments, the distal shaft is comprised of the same material as the proximal shaft.

With specific reference now to the drawings in detail, it is stressed that the particulars shown are by way of example and for purposes of illustrative discussion of certain embodiments of the present invention only. Before explaining embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
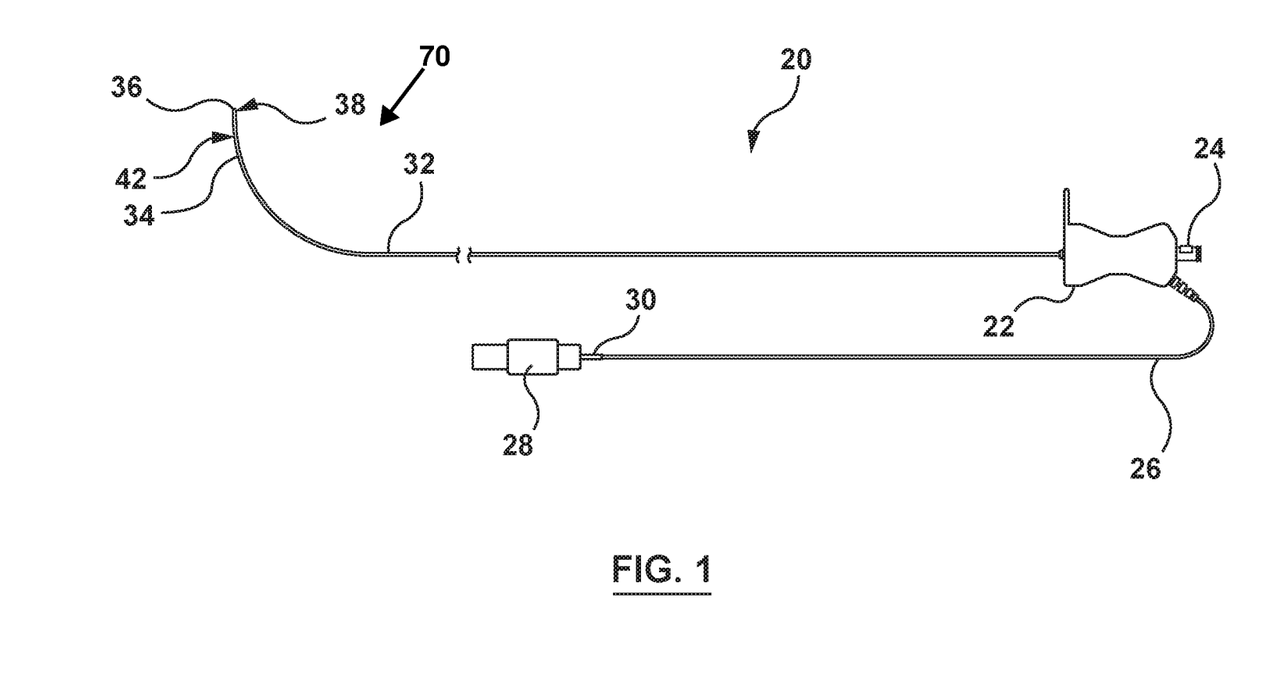
FIG. 1 is a top view of a needle assembly in accordance with an embodiment of the present invention.

FIG. 1 illustrates an assembly having a needle 20 that includes a proximal shaft 32, a distal shaft 42, a distal curved section 34, and a distal end 38 having an atraumatic electrode 36. In the embodiment of FIG. 1, distal curved section 34 includes both proximal shaft 32 and a portion of distal shaft 42, while in some alternative embodiments, distal curved section 34 includes only distal shaft 42. In such embodiments, distal curved section 34 may comprise all or part of the distal shaft i.e. the distal shaft 42 comprises distal curved section 34. Needle 20 also includes a hub/handle 22 with an attached electrical cable 26, and a fluid input 24. Electrical connector 28 is connected to the end of electrical cable 26 with heat shrink 30 covering the connection. Further details regarding needles used for puncturing tissue are found in U.S. Pat. No. 8,192,425, "RADIOFREQUENCY PERFORATION APPARATUS", filed Oct. 1, 2007, which is incorporated by reference herein in its entirety.

Proximal shaft 32 and a distal shaft 42 together form an elongate member 70 which is made from electrically conductive material that is biocompatible. As used herein, 'biocompatible' refers to a material that is suitable for use within the body during the course of a surgical procedure. Such materials include stainless steels, copper, titanium and nickel-titanium alloys (for example, nitinol), amongst others. In typical embodiments, the proximal shaft 32 is made from stainless steel, such that it provides column strength for transmitting force, and the distal shaft 42 is made out of a nickel-titanium alloy, such as nitinol, such that it may provide flexibility to a distal portion of the elongate member 70. Embodiments wherein proximal shaft 32 is manufactured from stainless steel typically result in needle 20 having a similar amount of column strength to a device of the prior art, for example a mechanical perforator such as a Brockenbrough™ needle. This may be beneficial in that it may provide a familiar 'feel' to users who have used such devices in the past. In some embodiments comprising a distal curved section 34, the rectilinear section is made from stainless steel, such that it provides column strength to the elongate member 70, and the distal curved section 34 is made out of a nickel-titanium alloy, such as nitinol, such that it provides flexibility to the elongate member 70. In addition, the use of nitinol for distal curved section 34 is advantageous as the superelastic properties of this material helps in restoring the shape of the distal curved section 34 after the distal curved section is straightened out, for example when placed within a dilator.

The elongate member 70 has an electrical insulator 48 disposed on the external surface thereof with the electrode 36 substantially deprived from the electrical insulator 48. When a source of energy is coupled to the hub/handle 22 of the needle, the electrical insulator 48 substantially prevents leakage of energy along the length of the elongate member 70, thus allowing energy to be delivered from the electrode 36.

The electrical insulator 48 may be one of many biocompatible dielectric materials. Materials for electrical insulator 48 may include, but are not limited to, polytetrafluoroethylene (PTFE, Teflon®), parylene, polyimides, polyethylene terepthalate (PET), polyether block amide (PEBAX®), and polyetheretherketone (PEEK™), as well as combinations thereof. The thickness of the electrical insulator 48 may vary depending on the material used. Typically, the thickness of the electrical insulator is from about 0.02 mm to about 0.12 mm.

Figure 10:
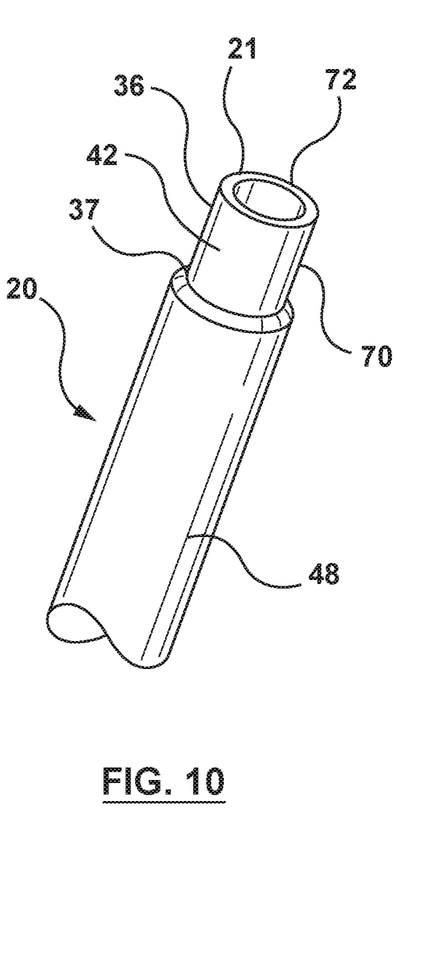
FIG. 10, in perspective view, shows an electrode configuration with an open end usable in the various embodiments of the needle.

In some embodiments, the electrode 36 is located at the distal end of distal shaft 42, for example by being mechanically coupled to the distal shaft, while in other embodiments the electrode 36 is integral with the distal shaft 42. In some embodiments of needle 20, the electrode 36 is comprised of superelastic material, while in other embodiments, the electrode is comprised of non-superelastic material. In some specific embodiments, the electrode 36 is comprised of a non-superelastic material and is mechanically coupled to the distal shaft 42. In the example of FIG. 10, the electrode 36 comprises the distalmost portion of the distal shaft 42 of elongate member 70. That is, as shown in FIG. 10, if the electrical insulator 48 extends to a point that is substantially adjacent to the distal end 72 of the elongate member 70 (i.e. to the distal end 37 of the insulation), the exposed distalmost portion of elongate member 70 is operable as the electrode 36. In the embodiment of FIG. 10, the distal end 72 of the elongate member 70 includes the distal tip 21 of needle 20. In this embodiment, the electrode 36 is shaped as a hollow ring or cylinder. Having an open distal end 72, as shown in FIG. 10, may be desirable to allow for addition and/or removal of material from a site within a patient's body.

Figure 11:
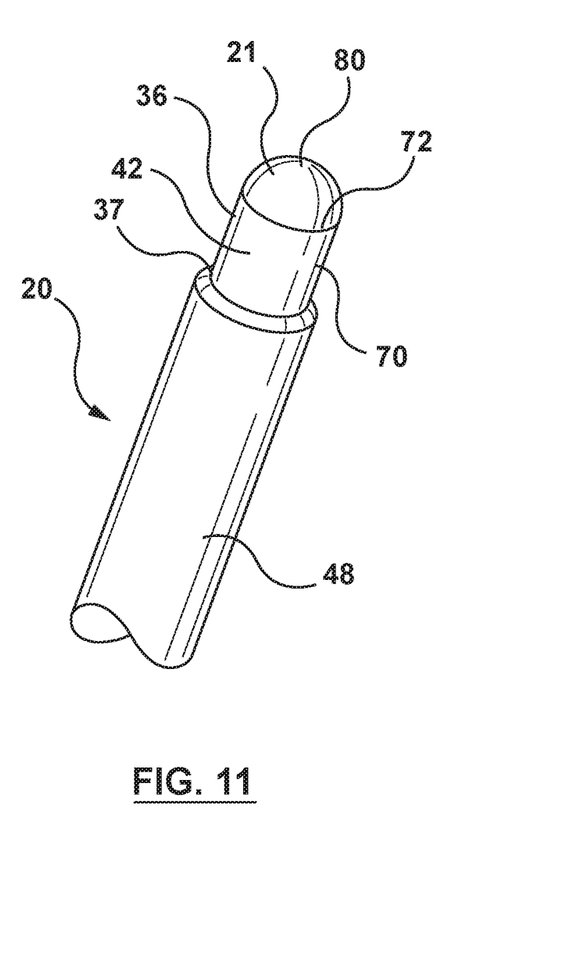
FIG. 11, in perspective view, shows an electrode configuration with an external component end usable in the various embodiments of the needle.

In further embodiments, such as shown in FIG. 11, the distal end 72 of the elongate member 70 is closed. For example, in some embodiments, it may be desirable for fluids to be injected radially from the elongate member 70, for example through side-port apertures in elongate member 70, substantially without being injected distally from the elongate member 70. In these embodiments, a closed distal end 72 may facilitate radial injection of fluid while preventing distal injection.

As shown in FIG. 11, an external component 80, for example an electrode tip, may be operatively coupled to the distal end 72. In this embodiment, the exposed portion of the distal region of distal shaft 42, as well as the external component 80, serves as the electrode 36. In the embodiment of FIG. 11, the external component 80 includes the distal tip 21 of needle 20. In some alternative embodiments, e.g. distal shaft 42 is closed-ended hypotube, the distal end 72 of elongate member 70, rather than a separate external component, is closed and is operable as the electrode 36. In other alternative embodiments, a metal plug (or metal particles) is placed in the distal end of a hollow distal shaft 42, and the distal shaft and plug are welded to thereby fuse them together.

Figure 2:
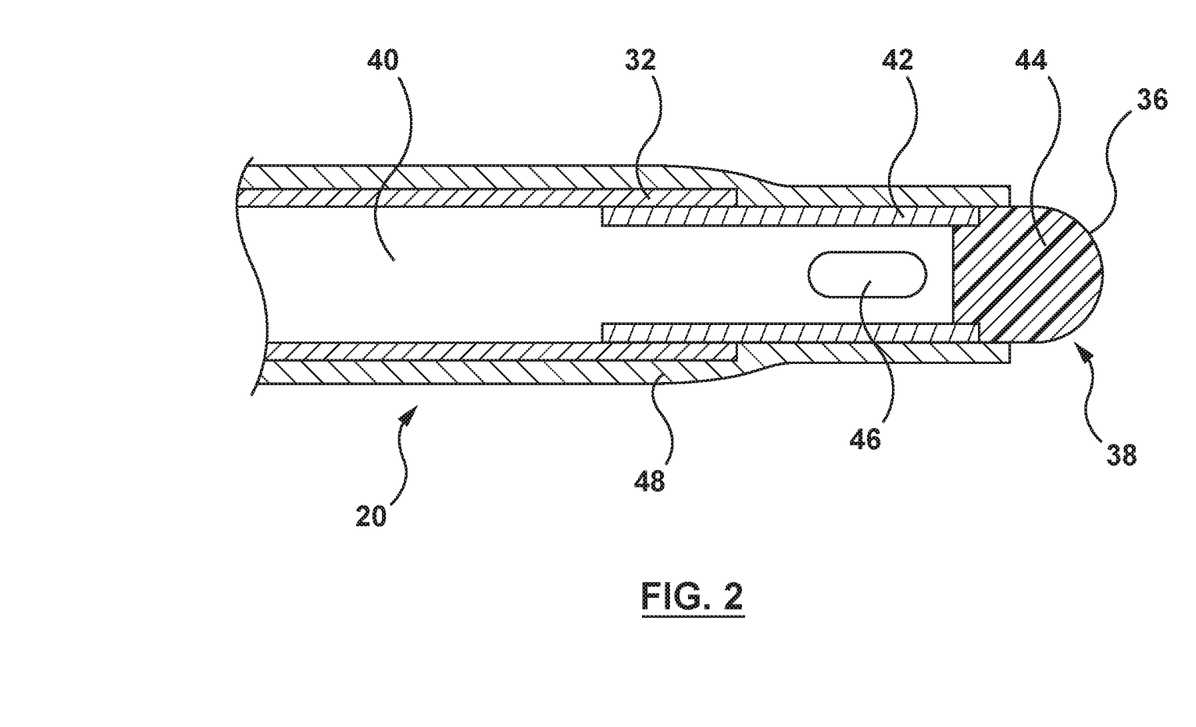
FIG. 2 is a cross-sectional side view of the distal portion of a needle having an overlapping tube configuration in accordance with an embodiment of the present invention.

FIG. 2 illustrates a cross sectional side view of the distal portion of a needle 20 having a proximal shaft 32 comprised of a material that provides columnar strength for pushability (e.g. stainless steel or titanium), and a distal shaft 42 comprised of a superelastic material (e.g. a nickel-titanium alloy or a titanium-niobium-tin (TiNbSn) alloy). Under normal use, the superelastic material of the distal shaft 42 bends and returns to its original shape without permanently deforming. Distal shaft 42 typically forms a smooth radius (i.e. a smooth curve) when subjected to a mechanical load. In typical embodiments of needle 20, proximal shaft 32 is comprised of a rigid metal and distal shaft 42 is comprised of a biocompatible superelastic metal known to those skilled in the art. In a specific embodiment, proximal shaft 32 is comprised of stainless steel having a modulus of elasticity of about 180 to 200 GPa, and distal shaft 42 is comprised of a nickel-titanium alloy (e.g. Nitinol®) having a modulus of elasticity of about 40 to 75 GPa.

The embodiment of distal shaft 42 of FIG. 2 is substantially straight, while that of FIG. 1 has a curve. In some alternative embodiments, the distal portion of distal shaft 42 has a partial spiral shape (or pigtail shape) when the needle 20 is not being manipulated that may be used to anchor the distal end 38 of the needle in a location in a patient's body, for example, in the left atrium. In embodiments with a distal curved section 34, the partial spiral will form a curve within a curve.

The embodiment of FIG. 2 further includes electrical insulator 48 outside of the proximal and distal shafts, leaving electrode 36 electrically exposed. An aperture or side-port 46 is in fluid communication with lumen 40, whereby the needle 20 may be used for delivering fluid, withdrawing fluid, and/or monitoring pressure. In some embodiments, electrode 36 is comprised of a radiopaque material to provide an imaging marker 44 for positioning the distal end 38 of the device.

In some embodiments, proximal shaft 32 has a length of about 50 cm to about 100 cm, and an outer diameter of about 1.15 mm to about 1.35 mm. In some embodiments, the distal shaft 42 has a length of about 2.5 cm to about 10 cm, and an outer diameter of about 0.40 mm to about 0.80 mm. Further details regarding needles used for puncturing tissues and the curves in such needles are found in U.S. Pat. No. 8,679,107, "RADIOFREQUENCY PERFORATION APPARATUS", filed May 10, 2012, which is herein incorporated-by-reference in its entirety.

Making reference to FIGS. 1 and 2, some embodiments of needle 20 include a distal curved section 34 having a tube-in-tube configuration wherein the proximal shaft 32 overlaps the distal shaft 42 such that the distal shaft is partially nested within the proximal shaft. In tube-in-tube embodiments in which distal curved section 34 includes both proximal shaft 32 and distal shaft 42, the curve of proximal shaft 32 and distal shaft 42 should have the same radius (i.e. the curves should be the same) across the overlap. In some specific embodiments, the curve has a radius of about 5.6 cm (about 2.2 inches). The proximal shaft 32 and the distal shaft 42 are substantially tubular and joined in any suitable manner, for example welding, soldering, friction fitting, or the use of adhesives, among other possibilities.

The usable needle length (i.e. the length of the needle's shaft that may be inserted into a patient's body) of such embodiments is the combined length of proximal shaft 32 and distal shaft 42 (after being joined) that extends distal to hub/handle 22. Some embodiments of needle 20 have a useable length of about 56 cm to about 98 cm. Some specific embodiments have useable lengths of about 56+0.5/−0 cm, 71±0.5 cm, 89±0.5 cm, or 98±0.5 cm. Some embodiments have a distal shaft 42 with a length of about 25 to 35 mm and some specific embodiments have a distal shaft of about 30±2 mm. In some embodiments of needle 20, distal shaft 42 extends about 13 to 17 mm distal of proximal shaft 32, and in some specific embodiments, distal shaft 42 extends about 15+1/−0 mm.

With respect to the diameters of needle 20, some embodiments comprise distal shaft 42 having an inner diameter of about 0.015 to 0.022 inches (0.38 to 0.59 mm), an outer diameter of about 0.023 to 0.029 inches (0.58 to 0.74 mm), and a proximal shaft 32 having an inner diameter of about 0.025 to 0.031 inches (0.64 to 0.79 mm), and an outer diameter of about 0.038 to 0.055 inches (0.97 to 1.4 mm). Some specific embodiments comprise distal shaft 42 having an inner diameter of about 0.017+0.001/−0.0005 inches (0.43+0.025/−0.013 mm), an outer diameter of about 0.025+ 0.0005/−0.000 inches (0.64+0.013/−0.0 mm), and a proximal shaft 32 having an inner diameter of about 0.027±0.0015 inches (0.69±0.038 mm), and an outer diameter of about 0.042+0.0005/−0.0 inches (1.1+0.012/−0.0 mm). Some other specific embodiments comprise distal shaft 42 having an inner diameter of about 0.020±0.0008 inches (0.51±0.020 mm), an outer diameter of about 0.028+ 0.0004 inches (0.71+0.010 mm), and a proximal shaft 32 having an inner diameter of about 0.028+0.002/−0.0 inches (0.71+0.051/−0.0 mm), and an outer diameter of about 0.047±0.0006 inches (1.2±0.015 mm).

In some alternative embodiments, distal end 38 comprises a sharp distal tip for mechanically puncturing tissue. Some alternative embodiments do not include a lumen or side-port (or aperture). Furthermore, some alternative embodiments comprise a single shaft comprised of a superelastic metal.

Figure 3:
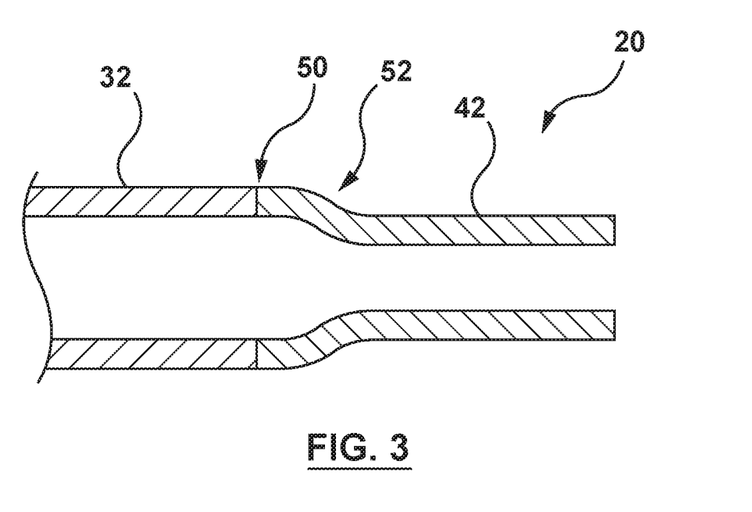
FIG. 3 is a cross-sectional side view of a tapered distal portion of a needle having an end-to-end tube configuration in accordance with an embodiment of the present invention.
Figure 4:
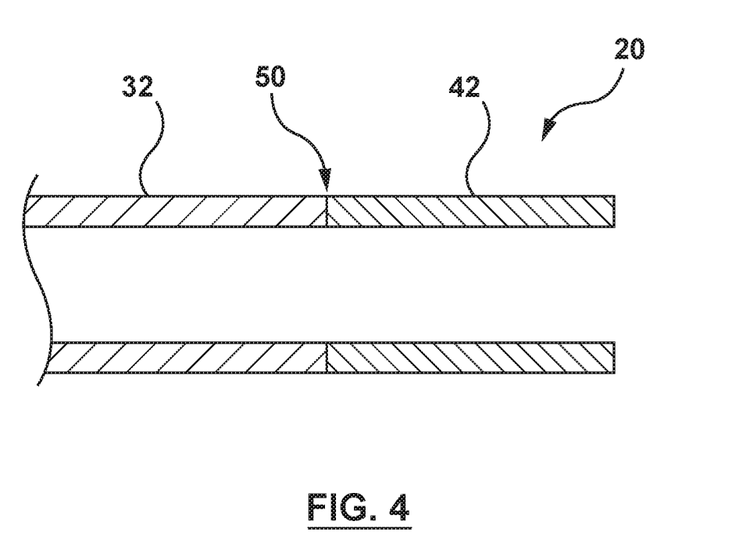
FIG. 4 is a cross-sectional side view of a non-tapered distal portion of a needle having an end-to-end tube configuration in accordance with an embodiment of the present invention.
Figure 5:
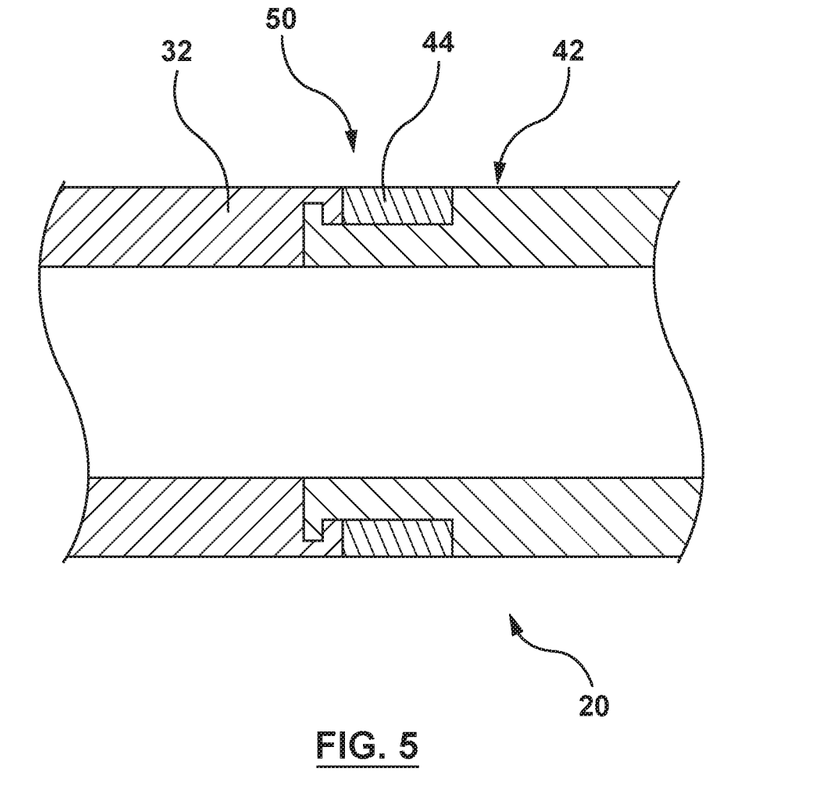
FIG. 5 is a cross-sectional side view of the distal portion of a needle having an interlocking joint in accordance with an embodiment of the present invention.

The embodiment of needle 20 in FIG. 2 has a tube-in-tube configuration wherein the inner diameter of proximal shaft 32 accommodates the outer diameter of distal shaft 42. FIGS. 3, 4, and 5 illustrate alternative tube configurations.

FIG. 3 shows a cross-sectional side view of the distal portion of a needle 20 wherein proximal shaft 32 and distal shaft 42 are joined at joint 50 and have an end-to-end tube configuration with a taper 52. FIG. 4 shows a needle 20 having an end-to-end tube configuration without a taper.

FIG. 5 shows a cross-sectional side view of the distal portion of a needle wherein the junction comprises an interlocking joint 50. The embodiment of FIG. 5 further includes an imaging marker 44 that the user may view under imaging to determine the location of the joint 50 within a patient's body. The distal shaft 42 and proximal shaft 32 may be joined by gluing, welding, or other means known to those skilled in the art. In one embodiment, curvatures are imparted into a superelastic distal shaft 42 using a thermal shape-setting process, and into a non-superelastic proximal shaft 32 using a mechanical process (i.e. a process without heating).

Figure 6:
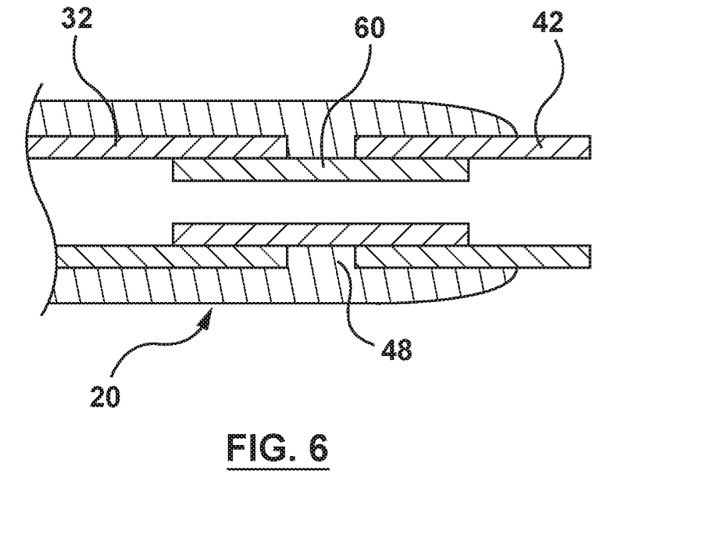
FIG. 6 is a cross-sectional side view of the distal portion of a needle having an overlapping hinge.
Figure 7:
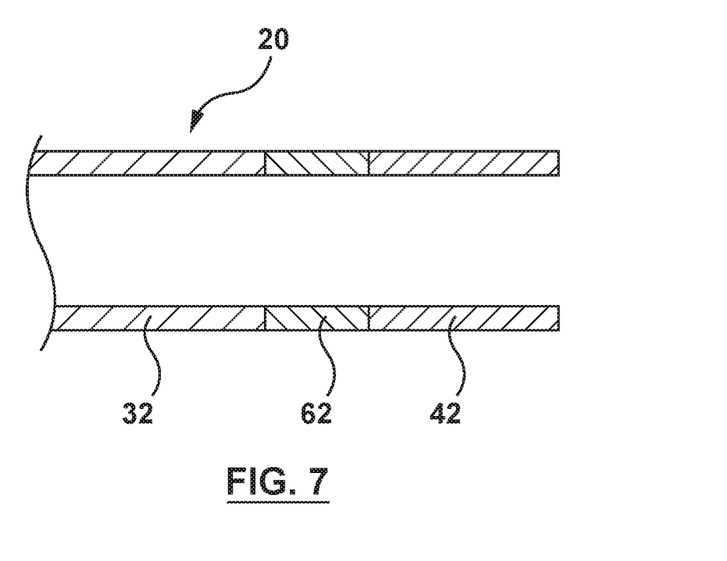
FIG. 7 is a cross-sectional side view of the distal portion of a needle having an end-to-end hinge.
Figure 8:
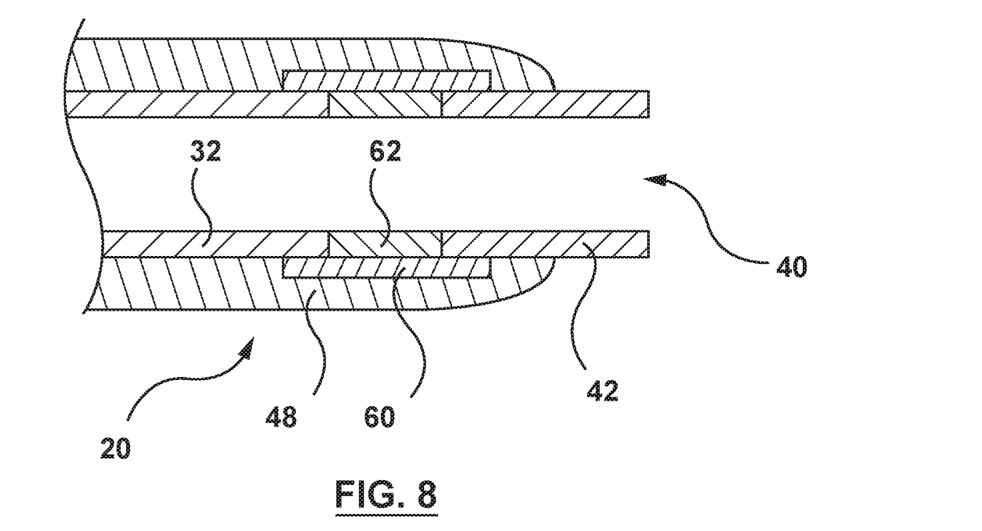
FIG. 8 is a cross-sectional side view of the distal portion of a needle having a combined overlapping and end-to-end hinge.

FIGS. 6, 7, and 8 illustrate embodiments of needle 20 comprising a proximal shaft 32 sufficiently rigid to provide pushability to the needle, a distal shaft 42 comprised of a non-superelastic material, and a superelastic hinge or bendable portion connecting or joining the proximal and distal shafts. In some embodiments, distal shaft 42 is comprised of the same material as proximal shaft 32.

FIG. 6 illustrates an embodiment of a needle including a junction comprising an overlapping superelastic hinge 60. Overlapping superelastic hinge 60 overlaps and is joined to proximal shaft 32 and distal shaft 42. The example of FIG. 6 includes electrical insulator 48 which is flowed into the space between proximal shaft 32 and distal shaft 42.

FIG. 7 is a cross-sectional side view of the distal portion of a needle having a junction comprising an end-to-end superelastic hinge 62 connecting the proximal and distal shafts.

FIG. 8 illustrates an embodiment of a needle having a junction comprising a combined overlapping and end-to-end superelastic hinge which includes an overlapping superelastic hinge 60 portion and an end-to-end superelastic hinge 62 portion. Overlapping superelastic hinge 60 portion is on the outside of the proximal and distal shafts, and electrical insulator 48 covers the shafts and hinges to provide a smooth outer surface. The overlapping portion and end-to-end portion may be the same material or different materials.

Figure 9:
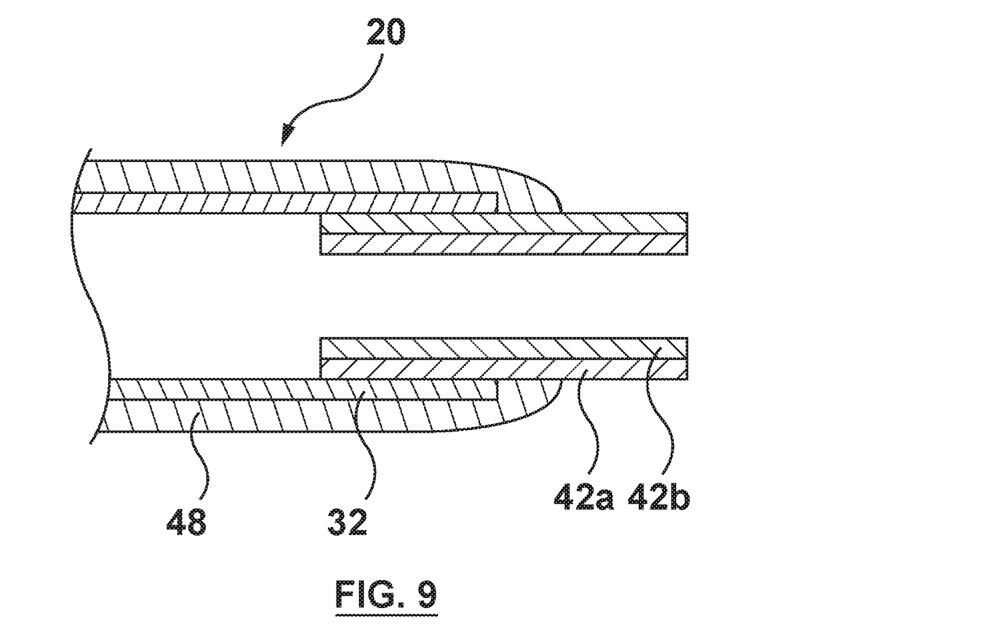
FIG. 9 is a cross-sectional side view of the distal portion of a needle having a hybrid distal shaft.

FIG. 9 is a cross-sectional side view of the distal portion of a needle having a hybrid distal shaft. Proximal shaft 32 is sufficiently rigid to provide pushability to the needle. The distal shaft 42 is comprised of an inner layer 42*b* and an outer layer 42a, with one layer being comprised of superelastic material and the other layer being comprised of non-superelastic material. While the embodiment of FIG. 9 includes inner layer 42b and outer layer 42a being about the same thickness, embodiments of the needle include the superelastic layer comprising from about 10 to 90 percent of the thickness of distal shaft 42. The thickness of the non-superelastic material may be varied to adjust the rigidity of the distal shaft. In some alternative embodiments, distal shaft 42 includes more than two layers of material.

The example of FIG. 9 includes the proximal and distal shaft having an overlapping tube-in-tube configuration. Some embodiments having the hybrid distal shaft comprise the proximal and distal shaft being joined in one of the other configurations described above, or other configurations know to those skilled in the art.

Figure 12:
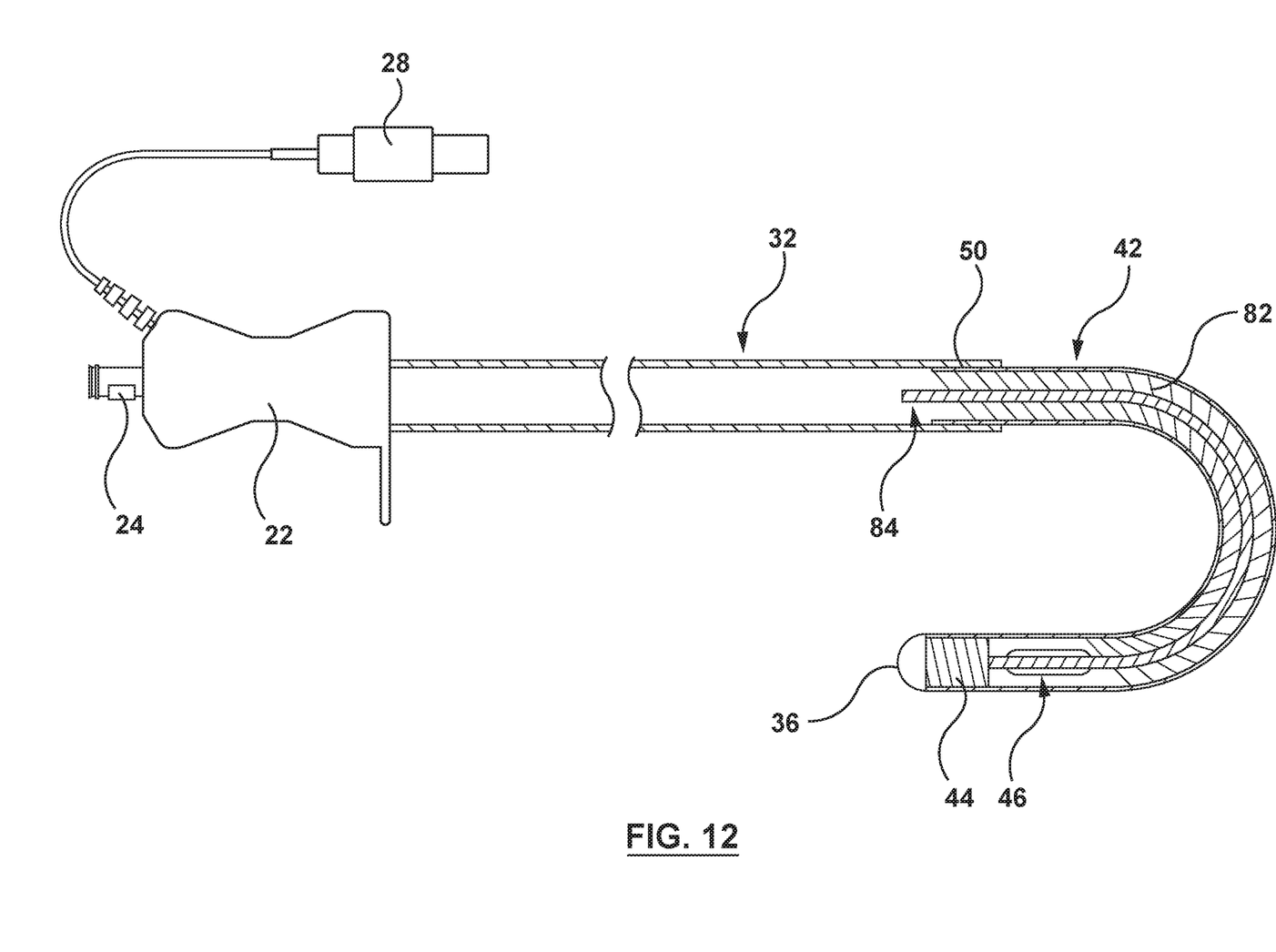
FIG. 12, in a partially cut-away view, illustrates an embodiment of the needle having an internal support wire.

FIG. 12, in a partially cut-away view, illustrates an embodiment of the needle 20 having an internal support wire 84 and a spiral cut 82 in distal shaft 42. Proximal shaft 32 and distal shaft 42 are joined at joint 50. In the embodiment of FIG. 12, proximal shaft 32 is typically made of stainless steel and support wire 84 is made of nitinol. Spiral cut 82 extends distally from joint 50 and stops proximally of side-port 46. Spiral cut 82 increases the flexibility of distal shaft 42. In some embodiments, distal shaft 42 is comprised of a continuously laser-cut nitinol hypotube. While the proximal shaft 32 of FIG. 12 is straight, in some alternative embodiments it includes a curved portion or a bend for increased torqueability. The distal shaft 42 of FIG. 12 is curved (when not forced into another shape), but some alternative embodiments of distal shaft 42 are straight or have other curved configurations.

In FIG. 12, support wire 84 extends proximally from imaging marker 44. In some alternative embodiments without imaging marker 44, support wire 84 extends proximally from electrode 36. In general, support wire 84 extends proximally from a distal end 38 of the needle at least within the lumen of distal shaft 42. Support wire 84 provides support for distal shaft 42. Support wire 84 can be made of steel, nitinol, or other metals, and is typically concentrically aligned with distal shaft 42. In some embodiments, distal shaft 42 and support wire 84 are both comprised of a superelastic material such as nitinol to provide for shape retention. Details about the support wire 84 and spiral cut 82 are found in U.S. application Ser. No. 14/851,353, entitled "Electrosurgical device having a lumen", filed Sep. 11, 2015, and U.S. application Ser. No. 14/851,412, entitled "Medical device having a support structure", filed September 11, which are incorporated by reference herein in their entirety.

The transverse cross-sectional shape of the elongate member 70 (proximal shaft 32 and distal shaft 42) of the different embodiments may take any suitable configuration, and the invention is not limited in the regard. For example, the transverse cross-sectional shape of embodiments of the elongate member 70 is substantially circular, ovoid, oblong, or polygonal, among other possibilities. Furthermore, the cross-sectional shape may vary along the length of the elongate member. For example, in one embodiment, the cross-sectional shape of the proximal region is substantially circular, while the cross-sectional shape of the distal region is substantially ovoid.

In one broad aspect, needle 20 is usable to deliver energy to a target site within a body of a human or animal to perforate or create a void or channel in a material at the target site. Further details regarding delivery of energy to a target site within the body are found in U.S. patent application Ser. No. 10/347,366 (filed on Jan. 21, 2003), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003) and U.S. Pat. No. 6,565,562 (issued on May 20, 2003), all of which are incorporated herein by reference.

In one specific embodiment, the target site may comprise a tissue within the heart of a patient, for example, the atrial septum of the heart. In such an embodiment, the user may access the target site from the inferior vena cava (IVC) via the femoral vein. In alternative embodiments, the needle may be used to puncture or provide a channel through a graft material or a blockage of an anatomical lumen.

In other embodiments, methods of the present invention may be used for treatment procedures involving other regions within the body, and the invention is not limited in this regard. For example, rather than the atrial septum, embodiments of devices, systems and methods of the present invention may be used to treat pulmonary atresia. In some such embodiments, a sheath is introduced into the vascular system of a patient, and guided to the heart. A dilator is then introduced into the sheath, and advanced towards the heart, where it is positioned against the pulmonary valve. Needle 20 is then introduced into the proximal region of the dilator, and guided therethrough, such that it is also positioned against the pulmonary valve. Energy is then delivered from the energy source, through the electrode 36 of needle 20, to the pulmonary valve, such that a perforation or void is created therethrough, as described hereinabove. When the needle has passed through the valve, the user may apply a force, for example in a substantially cranial direction, to the proximal region of the dilator. The force may be transmitted to the distal region of the dilator, such that the distal region of the dilator enters the perforation and advances through the pulmonary valve. As regions of the dilator of larger diameter pass through the perforation, the perforation or channel becomes dilated.

In other applications, embodiments of a device of the present invention may be used to create voids or channels within or through other tissues of the body, for example within or through the myocardium of the heart. In other embodiments, the device may be used to create a channel through a fully or partially occluded lumen within the body. Examples of such lumens may include, but are not limited to, blood vessels, the bile duct, airways of the respiratory tract and vessels and/or tubes of the digestive system, the urinary tract and/or the reproductive system. In such embodiments, the device may be positioned such that the electrode of the device is substantially adjacent the material to be perforated. Energy may be delivered from an energy source, through the electrode 36, to the target site such that a void, perforation, or channel is created in or through the tissue.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A needle comprising a tubular distal shaft and a tubular proximal shaft joined at a junction to prevent movement of the tubular distal shaft and the tubular proximal shaft relative to each other, the tubular distal shaft and the tubular proximal shaft defining a lumen, the tubular distal shaft having an open distal end, the tubular distal shaft of the needle having a distal tip which includes an electrode for delivering energy to puncture a tissue, the electrode occluding the open distal end of the tubular distal shaft, wherein the tubular distal shaft is comprised of a superelastic material and the tubular proximal shaft is comprised of a non-superelastic material for providing columnar strength for pushability to enable advancement of the needle through a puncture in the tissue, wherein the junction comprises a proximal end portion of the tubular distal shaft overlapping with and being inside of a distal portion of the tubular proximal shaft to form an overlap.

2. The needle of claim 1, wherein the tubular proximal shaft is comprised of stainless steel or titanium.

3. The needle of claim 1, wherein the tubular distal shaft is comprised of a nickel-titanium alloy or a titanium-niobium-tin (TiNbSn) alloy.

4. The needle of claim 1, wherein the tubular proximal shaft is comprised of stainless steel having a modulus of elasticity of about 180 to 200 GPa, and the tubular distal shaft is comprised of a nickel-titanium alloy having a modulus of elasticity of about 40 to 75 GPa.

5. The needle of claim 1, further including an electrical insulator on an external surface of the tubular proximal shaft and the tubular distal shaft, leaving the electrode electrically exposed.

6. The needle of claim 1, wherein the tubular distal shaft defines a side-port in fluid communication with the lumen, whereby the needle is operable for delivering fluid, withdrawing fluid, and monitoring pressure.

7. The needle of claim 1, wherein the electrode comprises an external component which is operatively coupled to the distal tip of the tubular distal shaft.

8. The needle of claim 1, wherein the electrode comprises a metal plug which is located in the open distal end of the tubular distal shaft.

9. The needle of claim 1, wherein the junction comprises an interlocking joint.

10. The needle of claim 1, further comprising a spiral cut in the tubular distal shaft for increasing a flexibility of the tubular distal shaft.

11. The needle of claim 10, further comprising a support wire extending proximally from a distal end of the needle to at least within the lumen of the tubular distal shaft.

12. The needle of claim 1, wherein the tubular proximal shaft and the tubular distal shaft have an end-to-end tube configuration.

13. The needle of claim 1, wherein the tubular distal shaft is comprised of both the superelastic material and the non-superelastic material.

14. The needle of claim 13, wherein the tubular distal shaft is comprised of an inner layer and an outer layer, wherein one of the inner layer or the outer layer is comprised of the superelastic material and the other of the inner layer or the outer layer is comprised of the non-superelastic material.

15. The needle of claim 1, wherein the electrode is comprised of a superelastic material.

16. The needle of claim 1, wherein the electrode is comprised of a non-superelastic material and is mechanically coupled to the tubular distal shaft.

17. The needle of claim 1, wherein the tubular proximal shaft and the tubular distal shaft are joined by at least one of welding, soldering, friction fitting and a use of adhesives.

18. A needle comprising a tubular distal shaft and a tubular proximal shaft joined at a junction to prevent movement of the tubular distal shaft and the tubular proximal shaft relative to each other, the tubular distal shaft and the tubular proximal shaft defining a lumen, the tubular distal shaft of the needle having a distal tip which includes an electrode for delivering energy to puncture a tissue, the tubular distal shaft comprising a closed-ended tube having a closed distal end, the closed distal end is operable to function as an electrode, wherein the tubular distal shaft is comprised of a superelastic material and the tubular proximal shaft is comprised of a non-superelastic material for providing columnar strength for pushability to enable advancement of the needle through a puncture in the tissue, wherein the junction comprises a proximal end portion of the tubular distal shaft overlapping with and being inside of a distal portion of the tubular proximal shaft to form an overlap.

19. The needle of claim 18, wherein the tubular distal shaft is a closed-ended hypotube.

* * * * *